US008163549B2

(12) United States Patent
Yao et al.

(10) Patent No.: US 8,163,549 B2
(45) Date of Patent: Apr. 24, 2012

(54) METHOD OF OBTAINING VIABLE SMALL TISSUE PARTICLES AND USE FOR TISSUE REPAIR

(75) Inventors: Jian Q Yao, Austin, TX (US); Victor Zaporojan, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

(21) Appl. No.: 11/613,250

(22) Filed: Dec. 20, 2006

(65) Prior Publication Data

US 2008/0153157 A1    Jun. 26, 2008

(51) Int. Cl.
    *C12N 5/00* (2006.01)
(52) U.S. Cl. .................................. 435/325; 424/426
(58) Field of Classification Search .................. None
    See application file for complete search history.

(56) References Cited

U.S. PATENT DOCUMENTS

| | | | |
|---|---|---|---|
| 4,522,096 A | 6/1985 | Niven, Jr. | |
| 4,642,120 A | 2/1987 | Nevo et al. | |
| 4,656,137 A | 4/1987 | Balassa | |
| 4,773,418 A | 9/1988 | Hettich | |
| 5,053,050 A | 10/1991 | Itay | |
| 5,269,785 A | 12/1993 | Bonutti | |
| 5,403,317 A | 4/1995 | Bonutti | |
| 5,461,953 A | 10/1995 | McCormick | |
| 5,577,517 A | 11/1996 | Bonutti | |
| 5,585,007 A | 12/1996 | Antanavich et al. | |
| 5,788,662 A | 8/1998 | Antanavich et al. | |
| 5,827,217 A | 10/1998 | Silver et al. | |
| 5,842,477 A | 12/1998 | Naughton et al. | |
| 5,964,805 A | 10/1999 | Stone | |
| 6,120,514 A | 9/2000 | Vibe-Hansen et al. | |
| 6,174,313 B1 | 1/2001 | Bonutti | |
| 6,248,114 B1 | 6/2001 | Ysebaert | |
| 6,662,805 B2 | 12/2003 | Frondoza et al. | |
| 6,886,568 B2 | 5/2005 | Frondoza et al. | |
| 7,134,437 B2 | 11/2006 | Bonutti | |
| 2002/0029055 A1 | 3/2002 | Bonutti | |
| 2002/0055755 A1 | 5/2002 | Bonutti | |
| 2003/0009147 A1 | 1/2003 | Bonutti | |
| 2004/0078077 A1 | 4/2004 | Binette et al. | |
| 2004/0078090 A1* | 4/2004 | Binette et al. | 623/23.76 |
| 2004/0097829 A1 | 5/2004 | McRury et al. | |
| 2004/0117033 A1 | 6/2004 | Frondoza et al. | |
| 2004/0172045 A1 | 9/2004 | Eriksson et al. | |
| 2004/0175690 A1 | 9/2004 | Mishra et al. | |
| 2004/0176787 A1* | 9/2004 | Mishra et al. | 606/167 |
| 2004/0219182 A1 | 11/2004 | Gomes et al. | |
| 2005/0038520 A1 | 2/2005 | Binette et al. | |
| 2005/0054595 A1 | 3/2005 | Binette et al. | |
| 2005/0064042 A1 | 3/2005 | Vunjak-Novakovic et al. | |
| 2005/0095666 A1 | 5/2005 | Jhavar et al. | |
| 2005/0113937 A1 | 5/2005 | Binette et al. | |
| 2005/0125077 A1 | 6/2005 | Harmon et al. | |
| 2005/0152882 A1 | 7/2005 | Kizer et al. | |
| 2005/0177249 A1 | 8/2005 | Kladakis et al. | |
| 2005/0196460 A1* | 9/2005 | Malinin | 424/548 |
| 2005/0222687 A1 | 10/2005 | Vunjak-Novakovic et al. | |
| 2005/0226856 A1 | 10/2005 | Ahlfors | |
| 2005/0234485 A1 | 10/2005 | Seegert et al. | |
| 2005/0288796 A1 | 12/2005 | Awad et al. | |
| 2006/0210643 A1 | 9/2006 | Truncale et al. | |
| 2006/0292131 A1 | 12/2006 | Binette et al. | |

FOREIGN PATENT DOCUMENTS

| | | |
|---|---|---|
| EP | 1410811 A1 | 4/2004 |
| EP | 1433423 A1 | 6/2004 |
| EP | 1535633 A1 | 1/2005 |
| EP | 1506790 A1 | 2/2005 |
| EP | 1537883 A2 | 6/2005 |
| EP | 2101681 | 8/2011 |
| GB | 2404607 A | 9/2005 |
| WO | WO97/11090 | 3/1997 |
| WO | 02080991 A2 | 10/2002 |
| WO | WO2004/078032 A2 | 9/2004 |
| WO | 2004105576 A2 | 12/2004 |
| WO | 2006002253 A2 | 1/2006 |
| WO | WO-2006002253 A3 | 1/2006 |
| WO | WO 2006/090372 A2 * | 8/2006 |

OTHER PUBLICATIONS

Marcacci et al., Clinical Orthopaedics & Related Research, Jun. 2005, No. 435, p. 96-105.*
Xu et al., Plast. Reconstr. Surg., 2004, vol. 113, p. 1361-1371.*
Lu et al., Journal of Orthopaedic Research, May 2006, vol. 24, No. 6, Abstract.*
Hunziker et al., Osteoarthritis and Cartilage, 2002, vol. 10, p. 564-572.*
Lu et al., Journal of Orthopaedic Research, May 2006, vol. 24, No. 6, p. 1261-1270.*
Convery, F.R., et al., The Repair of Large Osteochondral Defects. An Experimental Study in Horses, Clin. Orthrop., 1972, 253-262, 82.
Meachim, G., et al., Repair of the joint surface from subarticular tissue in the rabbit knee, J. Anat., 1971, 317-327, 109-2.

(Continued)

*Primary Examiner* — Kade Ariani
(74) *Attorney, Agent, or Firm* — Schwegman, Lundberg & Woessner, P.A.

(57) ABSTRACT

The invention provides a composition including isolated small living tissue particles, a method of making the tissue particles, and a method of using the composition to ameliorate a tissue defect. The tissue particles are composed of cells and their associated extracellular molecules and are sized, in certain embodiments, to be smaller than about 1 mm. Another aspect of the inventive tissue particles is the large percentage of viable cells. In certain embodiments, the tissue particles are made from cartilage and the composition may also contain additives such as adhesives, solutions, and bioactive agents.

36 Claims, 4 Drawing Sheets

OTHER PUBLICATIONS

Mitchell, N., et al., The Resurfacing of Adult Rabbit Articular Cartilage by Multiple Perforations through the Subchondral Bone, J. Bone Joint Surg., 1976, 230-233, 58A-2.

O'Driscoll, S.W., et al., The Repair of Major Osteochondral Defects in Joint Surfaces by Neochondrogenesis with Autogenous Osteoperiosteal Grafts Stimulated by Continuous Passive Motion. An Experimental Investigation in the Rabbit, Clin. Orthrop., 1986, 131-140, 208.

Brittberg, M., et al., Treatment of Deep Cartilage Defects in the Knee with Autologous Chondrocyte Transplantation, N. Engl. J. Med., 1994, 889-895, 331-14.

Johnson, L., Arthroscopic Abrasion Arthroplasty Historical and Pathologic Perspective: Present Status, Arthroscopy, 1986, 54-69, 2-1.

Pridie, K.A., A method of resurfacing osteoarthritic knee joints, J. Bone Joint Surg., 1959, 618-619, 41B-3.

Horas, U. et al., Autologous Chondrocyte Implantation and Osteochondral Cylinder Transplantation in Cartilage Repair of the Knee Joint: A Prospective, Comparative Trial, J. Bone Joint Surg. Am., 2003, 185-192, 85A-2.

Knutsen, G., et al., Autologous Chondrocyte Implantation Compared with Microfracture in the Knee. A Randomized Trial, J. Bone Joint Surg. Am., 2004, 455-464, 86A-3.

Berlet, G.C., et al., Treatment of Unstable Osteochondritis Dissecans Lesions of the Knee Using Autogenous Osteochondral Grafts (Mosaicplasty), Arthroscopy, 1999, 312-316, 15-3.

Yamashita, F., et al., The Transplantatoin of Autogeneic Osteochondral Fragment for Osteochondritis Dissecans of the Knee, Clin. Orthrop., 1985, 43-50, 201.

Mahomed, M.N., et al., The Long-Term Success of Fresh, Small Fragment Osteochondral Alografts Used for Intraarticular Post-Traumatic Defects in the Knee Joint, Orthopedics, 1992, 1191-1199, 15.

Fontana, A., et al., Cartilage Chips Synthesized with Fibrin Glue in Rhinoplasty, Aesth. Plast. Surg., 1991, 237-240, 15.

Passl, R., et. al., Using Fibrin to Glue and Flatten Cartilage, Beitr. Orthrop. Tramatol., 1989, 503-507, 36.

Albrecht, F., et al., Closure of Osteochondral Lesions Using Chondral Fragments and Fibrin Adhesive, Arch. Orthop. Trauma surg., 1983, 101:213-217.

Kaplonyi, G. et al., The use of fibrin adhesive in the repair of chondral and osteochondral injuries, Injury, 1988, 19, 267-272.

Homminga, G. N., et al., Perichondral grafting for cartilage lesions of the knee, J. Bone Joint Surg. (Br.), 1990, 72-B: 1003-1007.

Bruns, J. et al., Autologous rib perichondrial grafts in experimentally induced osteochondral lesions in the sheep-knee joint: morphological results, Virchows Archiv A Pathol Anat, 1992, 421:1-8.

Temenoff, J. S. et al., Review: tissue engineering for regeneration of articular cartilage, Biomaterials 21 (2000) 431-440.

Bayliss, Michael T. et al., The properties of proteoglycan prepared from human articular cartilage by using associative caesium chloride gradients of high and low starting densities, Biochem. J., vol. 232 (1985) 111-117, Great Britain.

Brittberg, Mats, Autologous Chondrocyte Transplantation, Clinical Orthopaedics and Related Research, vol. 367S (1999), S147-S155, Lippincott Williams & Wilkins, Inc.

Coster, D.J. et al., Diced cartilage grafts to correct enophthalmos, British Journal of Ophthamology, vol. 64 (1980), 135-136.

De Kleine, E. Hoyt, A Simplified Method for Handling of Diced Cartilage, Plast Reconstr. Surg., vol. 3 (1948), 95-102.

Fontana, Aldo et al., Cartilage Chips Synthesized with Fibrin Glue in Rhinoplasty, Aesth. Plast. Surg., vol. 15 (1991), 237-240.

Ghazavi, M.T. et al., Fresh Osteochondral Allografts for Post-Traumatic Osteochondral Defects of the Knee, J. Bone Joint Surg., 79-B (1997), 1008-1013.

Erol, O. Onur, M.D., The Turkish Delight: A Pliable Graft for Rhinoplasty, Plast. Reconstr. Surg., vol. 105 (2000), 2229-2241.

Hangody, Laszlo et al., Autogenous Osteochondral Graft Technique for Replacing Knee Cartilage Defects in Dogs, Autogenous Osteochondral Mosaicplasty—Orthopaedics Int'l. Ed., vol. 5, No. 3 (1997), 175-181.

Hurtig, M.B., Use of autogenous cartilage particles to create a model of naturally occurring degenerative joint disease in the horse, Equine Orthop., No. 6 (1988), 19-22.

Mainil-Varlet P. et al., Articular cartilage repair using a tissue-engineered cartilage-like implant: an animal study, Osteoarthritis Cartilage Suppl. A, vol. 9 (2001), S6-15.

Paccola, Cleber A.J. et al., Fresh Immature Articular Cartilage Allografts—A Study on the Integration of Chondral and Osteochondral Grafts Both in Normal and in Papain-Treated Knee Joints of Rabbits, Arch. Orthop. Traumat. Surg., vol. 93 (1979), 253-259.

Peer, Lyndon A., M.D., Diced Cartilage Grafts—New Method for Repair of Skull Defects, Mastoid Fistula and Other Deformities, Archives of Otolaryngology, vol. 38, No. 2 (1943), 156-165.

Peretti, Giuseppe M. et al., Cell-Based Tissue-Engineered Allogenic Implant for Cartilage Repair, Tissue Engineering, vol. 6, No. 5 (2000), 567-576.

Plenk Jr., H. et al., Articular Cartilage Transplants in Experiments and Clinical Practice, ACA, Acta Chirurgica Austriaca, vol. 29, No. 137 (1997), 2-4.

Stoksted, P. et al., Crushed cartilage in nasal reconstruction, J. Laryng. Otol., vol. 100 (1986), 897-906.

Wakitani, Shigeyuki et al., Repair of Rabbit Articular Surfaces with Allograft Chondrocytes Embedded in Collagen Gel, J. Bone Joint Surg., vol. 71-B (1989), 74-80.

Yamamoto, Etsuo et al., Use of Micro-Sliced Homograft Cartilage Plates in Tympanoplasty, Acta Otolaryngol., suppl. 419 (1985), 123-129.

Yiling Lu, Sridevi Dhanaraj, Ziwei Wang, Dino M. Bradley, Steven M. Bowman, Brian J. Cole, Francois Binette, Minced Cartilage Without Cell Culture Serves as an Effective Intraoperative Cell Source for Cartilage Repair, Journal of Orthopaedic Research, Jun. 2006, 1261-1270, Wiley Periodicals, Inc., Wilminton, DE, USA.

Respons filed in U.S. Appl. No. 10/374,772, Jan. 6, 2009, George Xixis, Boston MA, USA.

1.132 Declaration of Julia Hwang filed in U.S. Appl. No. 10/374,772, Jan. 5, 2009, Julia Hwang, Wayland, MA, USA.

Aston, Jayne E., et al., Repair of articular surfaces by allografts of articular and growth-plate cartilage, British Editorial Society of Bone and Joint Surgery 68 B(1):29 35 (1986).

Bacsich, P.; and Wyburn, G.M, The Significance of the Mucoprotein Content on the Survival of Homografts of Cartilage and Cornea, Department of Anatomy University of Glasgow, vol. LXII (1946) 322-329.

Bentley, George, et al., Homotransplantation of isolated epiphyseal and articular cartilage chondrocytes into joint surfaces of rabbits, Nature 230:385 388 (1971).

Buckwalter, J. A., Articular cartilage injuries, Clinical Orthopaedics and Related Research 402:21 37 (2002).

Chen, Frank S., et al., Repair of articular cartilage defects: part II treatment options, The American Journal of Orthopedics 28(2):88 96 (1999).

Craigmyle, M. B., Studies of cartilage autografts and homografts in the rabbit, British Journal of Plastic Surgery 8:93 100 (1955 1956) [online Mar. 24, 2005].

Dupertuis MD, S. Milton, Actual Growth of Young Cartilage Transplants in Rabbits, Archives of Surgery, vol. 43 (1941) 32-63.

Gibson, Thomas, et al., The long-term survival of cartilage homografts in man, British Journal of Plastic Surgery 11:177 187 (1958 1959).

Hunziker, E. B., Articular cartilage repair: basic science and clinical progress—a review of the current status and prospects; Osteoarthritis and Cartilage 10(6):432 463 (2002).

Leopold MD, G., Experimental Studies into the Etiology of Tumors, Archie. F. Path. Anat., vol. LXXXV, No. 2 (1981) 283-324.

Nixon, Alan J., et al., "New horizons in articular cartilage," Proceedings of the 47th Annual American Association of Equine Practitioners Convention [San Diego, California, Nov. 24 28, 2001] 47:217 226.

Nixon, Alan J., et al., Isolation, propagation, and cryopreservation of equine articular chondrocytes, American Journal of Veterinary Research (USA) 53(12):2364 2370 (1992).

Peretti, Giuseppe M., et al., In vitro bonding of pre-seeded chondrocytes, Sport Sciences for Health 2(1):29 33 (2007).

Peretti, Giuseppe M., et al., Cell-based bonding of articular cartilage: An extended Study, Wiley Periodicals, Inc. (2003).

Peretti, Giuseppe M., et al., Biomechanical analysis of a chondrocyte-based repair model of articular cartilage, Tissue Engineering 5(4):317 326 (1999).

Peretti, Giuseppe M., et al., Bonding of cartilage matrices with cultured chondrocytes: an experimental model, Journal of Orthopaedic Research 16(1):89 95 (1998).

Prudden MD, T. Mitchell, Experimental Studies on the Transplantation of Cartilage, The American Journal of the Medical Sciences, vol. LXXXI (1981) 360-370.

Robinson, Dror, et al., Regenerating hyaline cartilage in articular defects of old chickens using implants of embryonal chick chondrocytes embedded in a new natural delivery substance, Calcified Tissue International 46(4):246 253 (1990).

Silverman, Ronald P., et al., Injectable tissue-engineered cartilage using a fibrin glue polymer, Plastic & Reconstructive Surgery 103(7):1809 1818 (1999).

Specchia, Nicola, et al., Fetal chondral homographs in the repair of articular cartilage defects, Bulletin of the Hospital for Joint Diseases 54(4):230 235 (1996).

Yilmaz, Sarper, et al., Viability of Diced, Crushed Cartilage Grafts and the Effects of Surgicel (Oxidized Regenerated Cellulose) on Cartilage Grafts, Plastic & Reconstructive Surgery 108(4): 1054-1060 (2001).

Zah, F. WilhSort Des Tissus Implantes Dan L'Organisme, Cong Med Int De Geneve, Sep. 11, 1977 (Translation included).

Mainil-Varlet, P, et al., "Articular cartilage repair using a tissue-engineered cartilage-like implant: An animal study", Osteoarthritis Cartilage Suppl. A, vol. 9, No Document Available, (2001), 6-15.

PCT International Search Report mailed Apr. 18, 2008.

* cited by examiner

METHOD OF OBTAINING VIABLE SMALL TISSUE PARTICLES AND USE FOR TISSUE REPAIR

TECHNICAL FIELD OF THE INVENTION

Preparation and use of tissue particles, sized from various sources, to repair tissue defects such as orthopedic tissue defects.

BACKGROUND

Articular cartilage is a thin, smooth, low friction, gliding surface composed of hyaline cartilage with resiliency to compressive forces. While only a few millimeters thick, it has excellent wear characteristics. Its mechanical and structural capacity depends on the integrity of its extracellular matrix, in which chondrocytes are sparsely distributed throughout structural macromolecules including collagen, proteoglycans, and noncollagenous proteins. Although chondrocyte cells produce the extracellular matrix, they compose less than 5% of the wet weight of cartilage.

The composition and highly complicated interaction of these components make regeneration and replacement techniques challenging. For example, the lack of a direct blood supply and few cells distributed widely among a dense extracellular matrix leads to a limited healing ability of damaged articular cartilage. This has led to a wide variety of treatment approaches for defects, for example, in the knee, with varying levels of success.

Procedures such as drilling, abrasion, microfracture, and debridement provide symptomatic pain relief and improved function. Collectively, these procedures may be referred to as subchondral bone marrow stimulation techniques where the bone underlying the cartilage, which has a rich blood supply, is caused to bleed. The goal of such procedures is to mobilize mesenchymal stem cells from the blood to differentiate into chondrocyte-like cells that synthesize repair tissue. Once the vascularized cancellous bone is disrupted, a fibrin clot forms and pluripotent cells migrate into the area. These cells eventually differentiate into chondrocyte-like cells that secrete type I, type II and other collagen types, as well as cartilage specific proteoglycans, after receiving appropriate mechanical and biological cues. The cells produce a fibroblastic repair tissue that on appearance and initial biopsy can have a hyaline-like quality, but over time, is demonstrated histologically as being predominantly fibrocartilaginous tissue. Fibrocartilage is a relatively disorganized lattice of collagen fibers, as opposed to the natural hyaline cartilage, and thus partially fills the defect with structurally weak tissue that also exhibits limited durability.

Other procedural options such as periosteal grafting, osteochondral autografts and allografts, and autogenous chondrocyte cell implantation have been used to repair cartilage defects for the purpose of reducing pain and restoring function. The success of these procedures generally diminishes over time, possibly due to formation of fibrocartilage, inadequate development of repair tissue, poor cell differentiation, and/or poor bonding to the surrounding articular cartilage borders. Intact full thickness grafts, such as osteochondral autografts and allografts, also may suffer from mismatched sizes, immunologic rejection, and poor adhesion of cartilage to bony surfaces. For autogenous chondrocyte cell implantation, two surgeries are required: chondrocytes are first obtained from an uninvolved area of cartilage and cultured for 14 to 21 days, then the cultured cells are injected into the defect exposed via an open incision and covered with a periosteal flap excised from the proximal medial tibia.

Various methods of promoting tissue growth and repair, and in particular cartilage repair, have been suggested and include the use of tissue particles derived from grinding non-demineralized, articular cartilage into pieces of about 60 μm to about 500 μm (Malinin U.S. patent application No. 20050196460); mincing tissue into particles using two parallel blades, resulting in particles of about 0.1 to about 3 mm$^3$ in size and containing at least one viable cell (Binette et al. U.S. patent application No. 20040078090); pulverizing soft tissue into morsels of about 1 to about 100 μm that may then be combined with viable elements (cells) and/or bioactive molecules (Awad et al. U.S. patent application No. 20050288796); and, milling allograft cartilage, which is then lyophilized to create particles in the size of about 0.01 mm to about 1 mm that can be formulated into a paste (Gomes et al. U.S. patent application No. 20040219182). Various methods of tissue preparation have also been disclosed including a method of generating dermal tissue pieces of about 50 μm to about 1500 μm using a roller with multiple blades (Mishra et al. U.S. patent application No. 20040175690).

Cell and/or tissue viability for implants needs to be improved. For example, homogenizers used to generate tissue particles have resulted in about 5% of the cells remaining viable following homogenization. Enzymatic digestion, which is often used to generate cells for autogenous chondrocyte cell transplantation, results in poor cell viability following initial isolation.

Improved compositions and methods for repairing tissue defects and in particular, articular cartilage defects are desired.

SUMMARY OF THE INVENTION

One embodiment is a composition including isolated small tissue particles composed of cells and their associated extracellular molecules (e.g., proteins, polysaccharides, proteoglycans, etc.) known as the extracellular matrix (ECM). The tissue particles are sized such that in some embodiments, the particles have at least one dimension less than about 60 μm. In another embodiment, the particles have at least one dimension less than about 1 mm. In another embodiment, the particles are sized so that the volume is less than about 1 mm$^3$. In some embodiments, at least about 50% of the cells in the tissue particles are viable. In other embodiments, at least about 80% of the cells in the tissue particles are viable. In some embodiments, the composition may also contain additives such as adhesives, solutions, and bioactive agents. Examples of adhesives include fibrin glue, Tisseal (Baxter BioScience, Deerfield Ill.), and Surgicel (Johnson & Johnson, New Brunswick N.J.). Examples of bioactive agents include fibrinogen, thrombin, bone morphogenic proteins (BMP), insulin-like growth factors (IGF), transforming growth factors (TGF) including the beta form (TGFβ), platelet-derived growth factor (PDGF), and bone marrow aspirate.

Another embodiment is a method for creating small tissue particles whereby a tissue sample is positioned on a cutting device containing at least two blades in parallel in one embodiment, and at least three blades in parallel in another embodiment. In embodiments containing at least three blades, spacing between the blades may be uniform or may vary. The space between the blades may define a dimension of the particle. In one embodiment, at least one blade is curved. In another embodiment, at least two blades are not parallel. In one embodiment, the sizing apparatus comprises three blades mounted in parallel and separated by spacers having a width of about 60 µm. By changing the relative spatial relationship between the tissue sample and the cutting apparatus, cuts can be made in the horizontal, vertical, and coronal planes. Because the angle between these planes can be varied, the resulting tissue particle can be sized to a variety of shapes, including cubes, triangles, quadrilaterals, and other polygons.

Another embodiment is a method using the described compositions in ameliorating a tissue defect. In one embodiment, the defective tissue may be cartilage, bone, ligament, meniscus, tendon, muscle, nucleus pulposus, gingiva, annulus fibrosus, periosteum, perichondrium, fascia, and/or perineurium. In one embodiment, defects within articular cartilage are subjected to the method. In general, the method includes placing the isolated sized tissue particles into a tissue defect site. Retention of the tissue particles in the defect site is facilitated by the small particle size. In certain embodiments, retention of the tissue particles at the defect site may be enhanced by techniques such as microfracture and use of adhesives.

Another embodiment is a use of the inventive small tissue particles under cell culture conditions and, for example, as part of in vitro experimentation and/or to propagate cells in culture.

The method and composition will be further appreciated with reference to the following figures and description.

BRIEF DESCRIPTION OF THE DRAWINGS

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

DETAILED DESCRIPTION

Figure 1A:
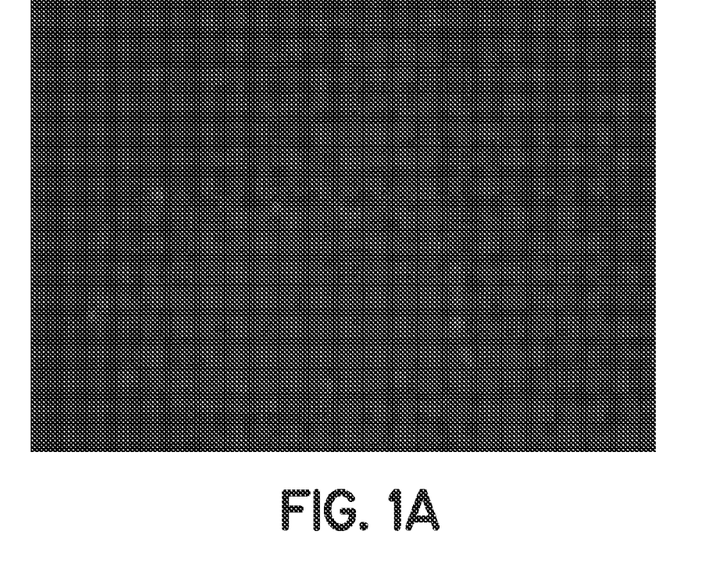
FIG. 1A is a photograph of particles with only live cell staining.
Figure 1B:
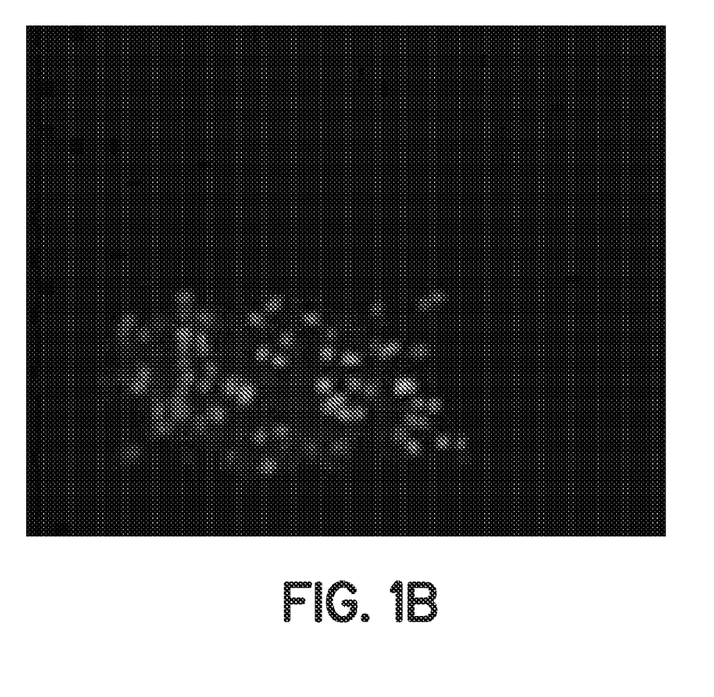
FIG. 1B is a photograph of particles with only dead cell staining.

In one embodiment, a composition comprising a plurality of isolated tissue particles is disclosed. The particles comprise cells and their associated extracellular molecules, (e.g. proteins, polysaccharides, proteoglycans, etc.), which collectively are termed a matrix. In another embodiment, the tissue particles are comprised of cells wherein at least about 50% of the cells are viable. In another embodiment, the tissue particles are comprised of cells wherein at least about 60% of the cells are viable. In another embodiment, the tissue particles are comprised of cells wherein at least about 65% of the cells are viable. In another embodiment, the tissue particles are comprised of cells wherein at least about 70% of the cells are viable. In another embodiment, the tissue particles are comprised of cells wherein at least about 75% of the cells are viable. In another embodiment, the tissue particles are comprised of cells wherein at least about 80% of the cells are viable. Cell viability indicates that the cell is alive and able to perform one or more intrinsic biological functions (e.g., cellular signaling, maintenance of cellular homeostasis, etc.), and also may include cells that are dormant or arrested in a stage of the cell cycle. Cells that are not viable are cells that are dead. The absolute number of viable cells may vary depending on, for example, the tissue type used to make the particles and/or particle size. The presence of viable cells in the tissue particle composition facilitates use of the composition in ameliorating tissue defects, as described more fully below. For example, viable cells provide stimulators and/or cues for tissue remodeling, growth, and/or repair. Methods to measure cell viability are known to one skilled in the art and include facilitated dyes and biochemical assays. For example, cell viability in the tissue particles was measured using the LIVE/DEAD® viability assay (Invitrogen, Eugene Oreg.) where the calcein dye is retained in live cells and emits a green fluorescence and the ethidium homodimer is able to enter cells with damaged membrane and emits red fluorescence when interacting with nucleic acids. FIG. 1A shows dead cells that emit red fluorescence in tissue particles in one embodiment of the invention. FIG. 1B shows living cells that emit green fluorescence in tissue particles in one embodiment of the invention. The results in FIGS. 1A and 1B showed satisfactory uptake of the dyes in to the small tissue particles.

Along with cells, the tissue particles also contain extracellular molecules, often referred to as the extracellular matrix (ECM). The ECM surrounds and supports cells within mammalian tissues, and is composed of three major classes of biomolecules: (i) structural proteins such as collagen and elastin; (ii) specialized proteins such as fibrillin, fibronectin, and laminin; and (iii) proteoglycans. Proteoglycans are composed of a protein core that is attached to long chains of repeating disaccharide units termed glycosaminoglycans (GAGs) and form complex high molecular weight components of the ECM. The ECM has many roles including cellular organization, guidance of cell migration and growth, and structure; the prominence of these roles can vary depending on the tissue. For example, the ECM plays an important role in force transmission and tissue structure maintenance especially in cartilage, tendons, ligaments, bone, and muscle. The precise composition of the ECM in the particles depends on factors such as the tissue from which the particles are obtained and any treatments or modifications thereof. Thus, the composition of the ECM will vary depending on the endogenous composition for that tissue type. Along with variations in ECM composition based on tissue type, the ECM may also be modified. As one example, the particles may be treated with bioactive proteins, such as BMP, IGF, TGF, PDGF, bone marrow aspirate, etc., to enhance the tissue repair ability of the particles. Also, the particles may be treated with enzymes that hydrolyze protein and/or glycans, such as trypsin and hyaluronidase, to increase the accessability of the ECM.

The size of the tissue particles of the inventive composition may vary depending on such factors as the type of source tissue used, the age of the tissue, and the intended subsequent use of the composition. In one embodiment, tissue particles are sized such that at least one dimension of the particle is less than 1 mm. In another embodiment, the tissue particles are sized such that at least one dimension is less than 60 µm. In another embodiment, the tissue particles are sized such that the particle is substantially cubical with each side about 60 µm or less. In another embodiment, the tissue is derived from a juvenile source and the tissue particles have a volume less than 1 mm$^3$. In another embodiment, the tissue particles have a volume of about 2×10$^{-4}$ mm$^3$. The tissue particles may be any shape, including but not limited to cubes and elongated strips. Sizing refers to cutting of the tissue sample into the desired size and/or shape, and is further described below.

The tissue particles may be derived from a variety of tissue types and tissue sources. The tissue may be autogenic, allogenic, or xenogenic with respect to the recipient of the inventive composition, as explained below. Any tissue is potentially suitable for use and tissue types may include cartilage, bone, ligament, meniscus, tendon, muscle, nucleus pulposus, gingival, annulus fibrosus, periosteum, perichondrium, fascia, and/or perineurium. In one embodiment, the tissue is articular cartilage. In another embodiment, the articular cartilage is hyaline cartilage and/or fibrocartilage.

In one embodiment, the tissue is engineered tissue. Engineering of the tissue refers to altering the physiology of the tissue such that it possesses traits that it would normally not have, magnifying and/or muting the existing tissue traits, and/or growing tissue in vitro. Engineered tissue may include tissue derived from a transgenic donor. Transgenic donor refers to tissue sources, such as animals, in which exogenous genetic material has been incorporated into the genome of the source. The incorporated genetic material may provide for the expression of a non-endogenous gene or may alter the expression levels of an endogenous gene. In another embodiment, the donor tissue may be genetically altered following removal from the donor. Examples of alterations of the tissue following excision and prior to or concomitant with culturing include alterations brought about by introduction of genetic material and/or bioactive agents. In the case of genetic manipulation, the tissue may be treated with genetic vectors using various methods of genetic introduction, e.g. viral- and lipid-mediated, as known in the art, to bring about alterations in endogenous or exogenous gene expression. Bioactive agents, such as growth factors, may be incubated with the cultured tissue to bring about alterations in tissue physiology. Engineered tissue may also refer to tissue that has been propagated or grown in vitro. Tissue grown in vitro refers to the creation and/or propagation of tissue outside an animal host. For example, in vitro grown tissue may result from tissue culture manipulations where cells are, for example, stimulated to form a tissue in an incubating vessel. Methods for producing in vitro tissue are known to one skilled in the art.

The developmental or maturation stage of the tissue used in the invention may also vary. For example, the tissue particles may be derived from embryonic, fetal, neonatal, juvenile, or adult tissue. In an embodiment where juvenile tissue is used, juvenile is defined as being less than 12 years old in the case of humans. Further, the tissue may be acutely isolated or cultured prior to sizing into particles. In the case of cultured tissue samples, the tissue is maintained in an environment that preserves the viability of the cells in the tissue. However, it is also understood by one skilled in the art that some cell death may occur as a result of in vitro tissue culturing. The tissue, either in preparation of culturing or following acute isolation, may be sized into smaller pieces that either facilitate subsequent sizing, e.g. results in a size that is easier to manipulate in the subsequent creation of tissue particles, or promotes cell viability in tissue culture, e.g. increases the surface area of the tissue and thus oxygen and nutrient accessibility to the cells. In another embodiment, the tissue is sized to the desired particle size prior to culture.

The composition may also include additional components. In one embodiment, the tissue particles of the composition are maintained or suspended in a solution. The solution may be a buffer that maintains the solution pH in a desired range. For example, the buffer may maintain the tissue particles in a solution in the range from about pH 6.8 to about pH 7.5. In other embodiments, the buffer may maintain the pH in the range of about pH 5 to about pH 7. The buffer, and the resulting buffering pH range chosen, depends on factors known to one skilled in the art including the tissue type and the effects of certain pH on that tissue type.

In another embodiment, the composition include bioactive agents. The bioactive agents may be either residual from culturing of the tissue sample as described above or may be added to the tissue particles at another time. Examples of bioactive agents include but are not limited to growth factors, hormones, and nutrients.

The inventive composition may also comprise an adhesive that aids in the attachment of the tissue particles to the site of tissue defect. The adhesive may be a naturally occurring bioadhesive such as fibrin. Thrombin converts soluble plasma fibrinogen into molecules of fibrin that polymerize and form a fibrin clot. Fibrin may encapsulate and/or enmesh the tissue particles at the sites of tissue defect. It should also be noted, however, that due to the small size of the inventive tissue particles, the particles are intrinsically adhesive to the site of tissue defect. In another embodiment, the tissue particles may be treated such that they become positively charged. The tissue particle may be charged by a variety of treatments including exposing the particles to an ionic detergent or a magnetic field, resulting in the creation of an overall positive charge on the particles. The overall positive charge of the particle facilitates adhesion of the particle to the predominantly negatively charged tissue defect. Increased adhesion of the particles to the tissue defect site may reduce the time required for tissue defect repair.

Figure 2:
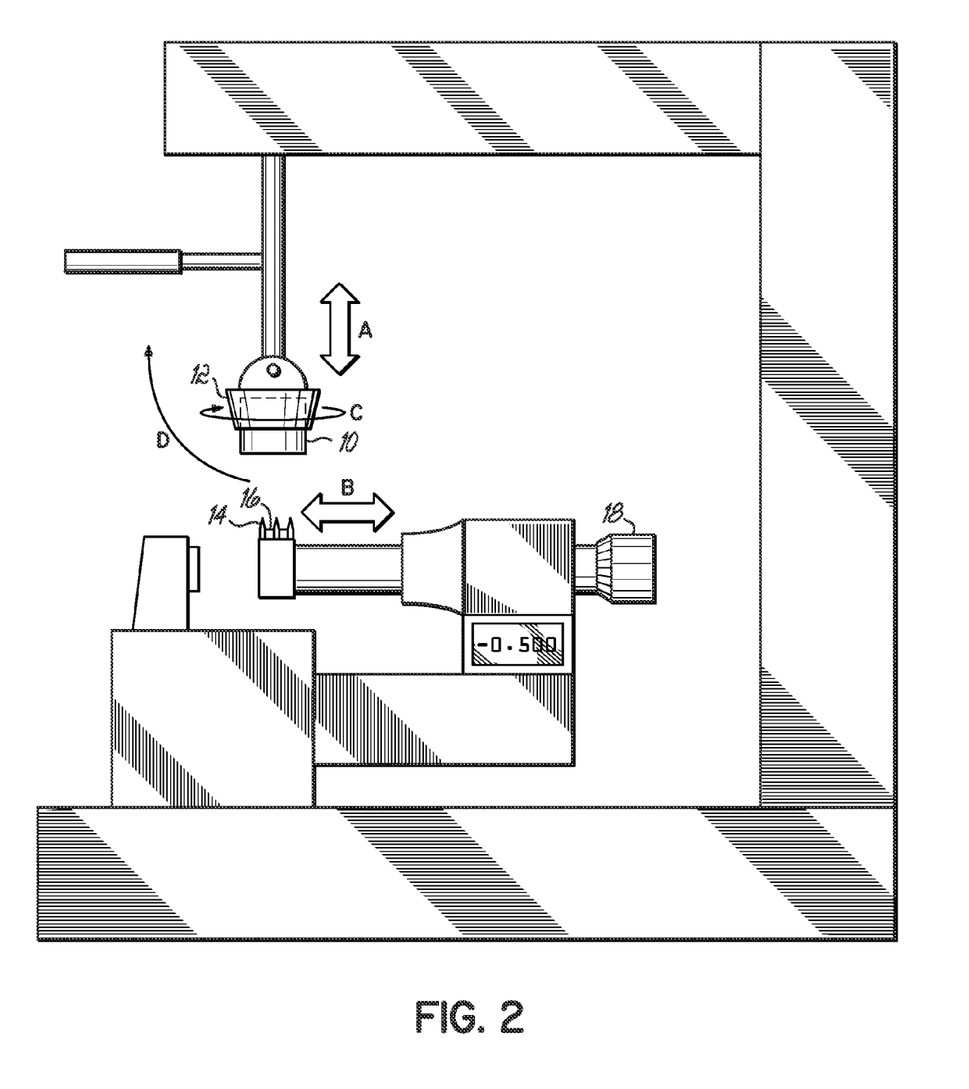
FIG. 2 shows an apparatus for sizing tissue particles.

In one embodiment, a method of preparing a composition comprising tissue sized into particles is disclosed. The tissue sample is initially cut into smaller pieces to facilitate subsequent sizing into tissue particles, e.g., using surgical tools known to one skilled in the art, such as a scalpel. In one embodiment, the tissue is initially cut into pieces of about 5 mm to about 11 mm. In another embodiment, the tissue, which may have been cultured, has already been subjected to the initial cutting process and is of the approximate size for subsequent sizing. As shown in the schematic of FIG. 2 (not to scale), once the tissue 10 is of the appropriate initial size, it is mounted on a jaw 12 of an axial cylinder. By extending the axial cylinder along axis A, the tissue 10 contacts the blades 14 mounted in opposition of the jaw. In one embodiment, the tissue is contacted with at least two blades mounted in parallel on a substantially flat surface. In another embodiment, the tissue is contacted with three blades mounted in parallel on a substantially flat surface. In another embodiment, the blades 14 are not parallel to each other and may also include blades that are not straight, e.g., curved. The configuration of blades 14 will also include spacers 16 between the blades, the width of which will correspond to the desired dimension between parallel cuts. In certain embodiments, the spacers 16 between the blades 14 will be the same size and in other embodiments, the spacers 16 may be of different sizes. The blades will be sufficiently sharp so that damage and/or loss of the tissue will be minimized.

Figure 3A:
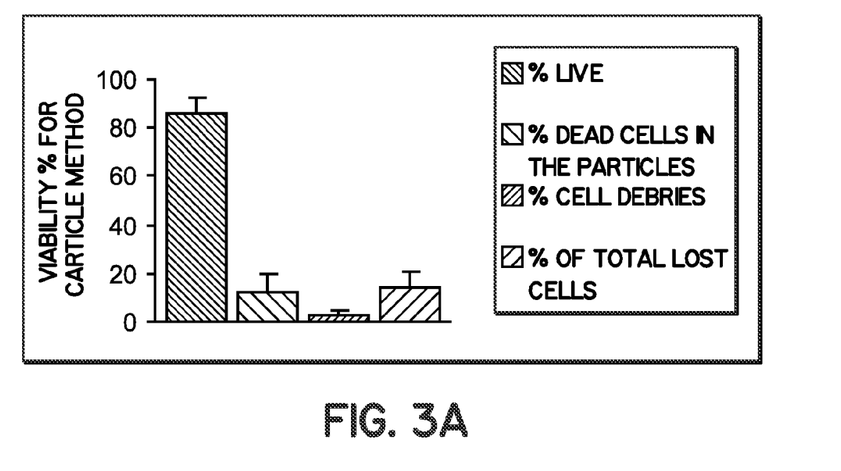
FIG. 3A shows the percentage of viable cells following one embodiment of the method.
Figure 3B:
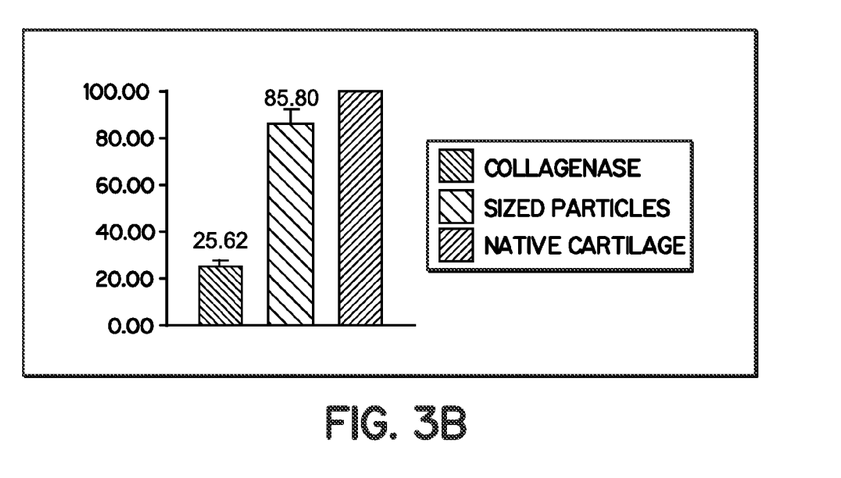
FIG. 3B shows the percentage of viable cells following enzymatic digestion versus an embodiment of the invention.

The method may be conducted in the absence of exogenously added digestive enzymes. Although digestive enzymes promote cell dissociation, they also may decrease the percent of viable cells resulting from the treatment. In FIG. 3, the viability of cells following one embodiment of the inventive method, as determined by LIVE/DEAD® viability assay, was about 85% (FIG. 3A) while viability of cells following enzymatic treatment with collagenase resulted in about 25% viable cells (FIG. 3B). Without being held to a single theory, it is believed that the digestive enzyme damages the cell membrane components, contributing to the death of the cell.

Figure 4:
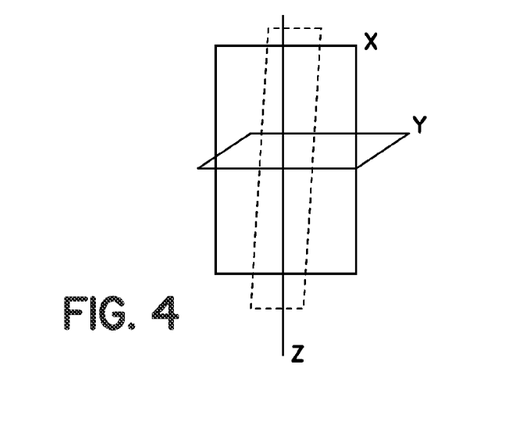
FIG. 4 shows a schematic representation of the three particle planes defined by the x-axis, y-axis, and z-axis.

The first contact between the blades and the tissue results in parallel cuts in, for example, the x-axis plane of the tissue sample, as shown in FIG. 4. In different embodiments, the tissue may be pushed against the blades or alternatively the blades may be pushed against the tissue. In another embodiment, the blade and tissue sample are both moved towards each other. In certain embodiments, the blades may not be parallel and therefore, would not result in parallel cuts. However, for simplicity, the inventive method will be described in terms of parallel blades making parallel cuts but in all cases, the blades and resulting cuts may not be parallel, and also may be non-straight, e.g., curved. Following the first contact between the blades and the tissue, the sample and/or blades can then be translationally moved along axis B. e.g. without rotation, so that further cuts can be made in parallel with the previous cuts and still in the same plane. In one embodiment, the blades are translationally moved with precision of about 1 µm using a digital micrometer 18, as shown in FIG. 2. The blades and/or tissue sample is then rotated relative to one another in rotation C about axis A, defining a second orientation and the blades and tissue are again caused to contact, making cuts in, for example, the y-axis plane, as shown in FIG. 4. In this second orientation, the blades and/or tissue can again be translationally moved so that a series of parallel cuts can be made. In one embodiment, the second contact between the blades and tissue results in substantially perpendicular cuts in the tissue wherein the angle between the first and second cut is about 90°. However, the angle between the first and second cuts may range from about 1° to about 179°. In one embodiment, the blades and/or the tissue sample are moved to achieve a third orientation wherein the blades cut the tissue sample in, for example, the z-axis plane, as shown in FIG. 4. The third orientation can be achieved by moving the tissue in direction D, as shown in FIG. 2. In one embodiment, the plane defined by this third orientation cuts the tissue substantially perpendicular to the plane of either the first or second cut, for example, the x-axis or y-axis plane, and results in a particle that is substantially cubicle. However, the angle between the third and either of the first or second cutting planes may range from about 1° to about 179°. Thus, by choosing the angles between the cut planes, the geometry of the resultant tissue particle can be varied.

Tissue particles of various sizes can be made by varying the size of the spacers between the blades and the angle between the cuts. In one embodiment, the tissue is cut using the procedure described above wherein three blades contact the tissue, the resultant tissue particle is sized such that at least one dimension is less than 60 µm. In another embodiment, the tissue is cut using the procedure described above wherein three blades contact the tissue and the tissue is derived from a juvenile, non-dermal source, the resultant tissue particle is sized such that at least one dimension is less than 1 mm. In another embodiment, the resultant tissue particle size is less than 1 mm$^3$. The method produces tissue particles of the desired dimensions and also maintained a high percentage, e.g. above about 85%, viable cells (See FIG. 3A).

As described above, the tissue source used by the inventive method to generate tissue particles may be used from any source and with any type of tissue including autogenic, allogenic, xenogenic, cultured, and engineered tissue and of any maturation stage.

In one embodiment, a method of ameliorating a damaged tissue in a mammal is disclosed. The tissue particle composition is introduced into or in proximity to a damaged tissue under conditions sufficient to ameliorate the damaged tissue. The composition may include a plurality of tissue particles sized from tissue. In addition, the particles may include both cells and extracellular molecules organized in a matrix, as described above. In one embodiment, the damaged tissue may be articular cartilage. In the case of damaged articular cartilage, the cartilage lesion may be debrided back to a stable base cartilage and loose or fibrillated cartilage may be resected. In one embodiment, in the case of articular cartilage, the subchondral base is microfractured until bleeding occurs from the subchondral bone. Microfracture entails creating a series of small fractures in the bone of about 3 mm to about 4 mm in depth using an awl. Alternatively, a drill may be used to create holes in the subchondral bone, with care to not cause heat necrosis in the site. The composition is applied into the area of and/or proximate the defect.

Figure 5A:
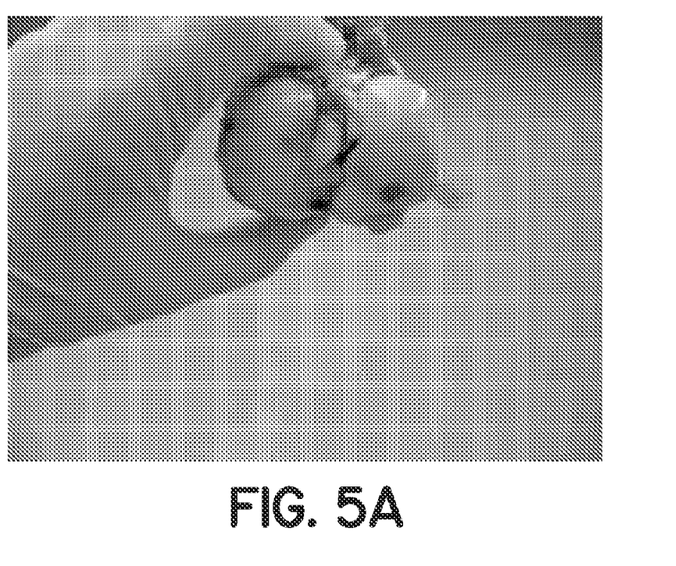
FIG. 5A shows a surface of a porcine knee joint that has been subjected to one embodiment of the invention.
Figure 5B:
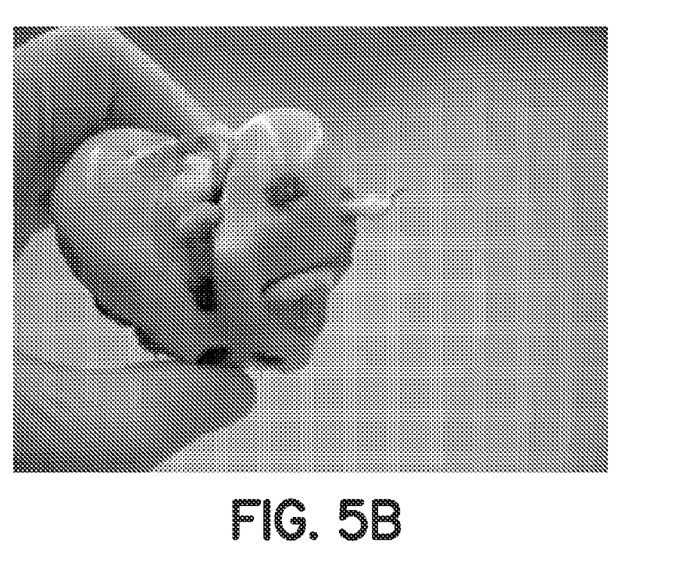
FIG. 5B shows a surface of a porcine knee joint that has been subjected to another embodiment of the invention.

In one embodiment, the method of ameliorating damaged tissue also includes adhering the inventive composition to the damaged tissue. If the method is conducted in conjunction with microfracture, adhesive properties of bleeding bone secure the tissue particles in place, as shown in FIG. 5A. Specifically, the resulting blood clot from the bleeding bone serves as a biological glue that maintains the particles on the surface near the defect. Also, due to the small size of the tissue particles, the particles naturally remain in the defect, as shown in FIG. 5B, possibly as a result of surface tension. The inventive composition may also include adhesives such as fibrin, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, MATRIGEL® (BD Biosciences, San Jose Calif.), monostearoyl glycerol co-succinate (MGSA), monostearoyl glycerol co-succinate/polyethylene glycol (MGSA/PEG) copolymers, laminin, elastin, proteoglycans, and combinations thereof.

In one embodiment, the tissue particles of the inventive composition may have been treated such that the particles exhibit a net charge, as described above, that facilitates electrostatic adhesion to the tissue defect. Other techniques known to one skilled in the art, such as flaps, may also be used to keep the particles in the defect site.

In one embodiment, the method is conducted using a minimally invasive procedure, e.g. arthroscopy. The use of a minimally invasive procedure allows a smaller incision, resulting in less pain, a shorter in-patient stay, and a faster recovery time than traditional more invasive procedures. The use of a minimally invasive procedure such as arthroscopy may also aid in diminishing potential post-operative complications such as soft tissue fibrosis.

In one embodiment, the damaged tissue may be orthopedic tissue such as cartilage, bone, ligament, meniscus, tendon, and/or other muscle. In another embodiment, the damaged tissue may be nucleus pulposus, gingival, annulus fibrosus, periosteum, perichondrium, fascia, and/or perineurium. In one embodiment, the damaged tissue and the tissue that is used as the source for the inventive composition are the same tissue type, e.g. articular cartilage. In another embodiment, the damaged tissue and the tissue that is used as the source for the inventive composition are different tissue types, including autogenic, allogenic, xenogenic, cultured, engineered tissue, and of any maturation stage.

One embodiment discloses a biocompatible implantable composition comprising a plurality of biological tissue particles sized from tissue derived from viable juvenile cartilage, wherein the particles are comprised of chondrocytes having at least about 80% viability and extrachrondrocyte proteins, each particle less than 60 μm, and the composition is capable of implantation in a mammal.

In one embodiment, particulate cartilage compositions are created and used for cartilage regeneration by stimulating chondrogenesis. Articular cartilage may be obtained from the articular surfaces of joints, such as from distal femurs, proximal tibia, acetabul, heads of femurs, and/or heads of radii, as well as from other sites where hyaline cartilage is present, e.g., auricular, nasal, temporomandibular joint, and costal margin. The cartilage may be removed, for example, with a scalpel blade, rongeur, or other surgical instrument. In one embodiment, cartilage is removed down to subchondral bone, without removing bone. The articular cartilage may include articular hyaline cartilage and/or fibrocartilage and may comprise allogeneic and/or xenogeneic cartilage.

The following example further illustrates embodiments of the invention.

EXAMPLE

Cartilage tissue particles were assessed for cell viability and evaluation in cartilage defect repair. All procedures were conducted in compliance with relevant regulations for the use of animal tissue. Porcine knee joints were obtained from a local abattoir. A knee joint was opened using a scalpel and the articular cartilage from the condyle load bearing area was exposed. Using a 7.5 mm diameter coring reamer, an osteochondral plug was obtained.

The osteochondral plug was mounted on the jaw of the cutting device (FIG. 2) and a series of cuts were made using three multiple blades to obtain viable small tissue particles.

Tissue particles were stained using LIVE/DEAD® stain to determine cell viability. The LIVE/DEAD® stain uses a membrane-permeant CALCEIN AM that is cleaved by endogenous esterases in the live cells to yield cytoplasmic green fluorescence, and the membrane-impermeant ethidium homodimer-1 labels nucleic acids of membrane-compromised cells, e.g. dead cells, with red fluorescence. Pictures of the stained slides were analyzed using NIH imaging software and the number of total and viable cells was calculated. For the enzymatic digestion method, cartilage was shaved off the articular surface and collected in a Petri dish. Tissue weight was recorded. The cartilage tissue blocks were digested in a 1:10 mass:volume ratio in 0.15% of collagenase type II for about 12-16 hours until no visible fragments remained. The cell-collagenase solution was filtered and washed with phosphate-buffered saline. Isolated cells were counted and viability was determined using LIVE/DEAD® staining. The number of viable cells was normalized to the tissue weight and represented as a percentage of the absolute number of cells in a given unit of tissue, as shown in FIG. 3A. Paired t-test statistical analysis was performed using Sigma Stat 2.0 software.

Results showed that tissue particles had a regular geometry. The majority of the particles were from 50 microns to 240 microns. LIVE/DEAD® staining experiments showed good tissue penetration of the dyes due to the size of the particles. Although a small percentage, about 10% to about 15%, of the tissue was lost during the cutting procedure, cell viability in the tissue particles was significantly higher than the percentage of viable cells obtained by digestion method (Compare FIGS. 3A and 3B). Tissue particles seeded on the surface of the joint remained attached to the surface against gravity for an indefinite period of time as long as conditions were maintained (FIG. 5B) and the adhesion was increased when microfracture was simulated by compressing the subchondral bone and causing to bleed (FIG. 5A).

The above results showed that small tissue living particles were obtained from an autologous source. The results also showed that cell viability inside of the particle remained higher than 85%.

It should be understood that the embodiments and examples described are only illustrative and are not limiting in any way. Therefore, various changes, modifications or alterations to these embodiments may be made or resorted to without departing from the spirit of the invention and the scope of the following claims.

What is claimed is:

1. A biocompatible implantable composition comprising a plurality of isolated viable tissue particles, the particles comprising cells having at least about 80% viability and cell-associated extracellular proteins, each particle sized to have at least one dimension less than 60 μm wherein the tissue is selected from the group consisting of cartilage, bone, ligament, meniscus, tendon, muscle, and combinations thereof.

2. The composition of claim 1 wherein the extracellular proteins are a component of an extracellular matrix.

3. A composition of claim 1 wherein the particles are isolated viable juvenile tissue particles.

4. The composition of claim 3 wherein extracellular proteins are a component of an extracellular matrix.

5. The composition of claim 3 wherein particles are sized to have at least another dimension less than 1 mm.

6. The composition of either claim 1 or claim 3 wherein the tissue is an engineered tissue.

7. The composition of either claim 1 or claim 3 wherein the tissue is articular cartilage.

8. The composition of claim 7 wherein the articular cartilage comprises at least one of hyaline cartilage or fibrocartilage.

9. The composition of either claim 1 or claim 3 further comprising at least one of an adhesive, a buffer, or a bioactive agent.

10. The composition of either claim 1 or claim 3 further comprising thrombin.

11. A method of preparing a biocompatible implantable composition comprising sizing an isolated viable tissue into particles using at least three blades mounted in parallel on a substantially flat surface so that each of the resulting particles has at least one dimension less than 60 μm wherein the tissue particles comprise a plurality of cells that are at least about 80% viable and cell-associated extracellular proteins organized in a matrix wherein the tissue is selected from the group consisting of cartilage, bone, ligament, meniscus, tendon, muscle, and combinations thereof.

12. A method of preparing a biocompatible implantable composition comprising sizing an isolated viable juvenile tissue into particles using at least three blades mounted in parallel on a substantially flat surface so that each of the resulting particles has at least one dimension less than 60 μm, wherein the tissue particles comprise a plurality of cells that are at least about 80% viable and cell-associated extracellular proteins organized in a matrix wherein the tissue is selected from the group consisting of cartilage, bone, ligament, meniscus, tendon, muscle, and combinations thereof.

13. The method of either claim 11 or claim 12 wherein the tissue is mounted in a jaw of an axial cylinder.

14. The method of either claim 11 or claim 12 further comprising pushing the tissue against the blades.

15. The method of either claim 11 or claim 12 wherein the tissue is sized at least twice.

16. The method of either claim 11 or claim 12 wherein a tissue orientation relative to the blade is varied to result in a plurality of particle shapes.

17. The method of either claim 11 or claim 12 wherein the tissue is at least one of autogenic, allogenic, or xenogenic.

18. The method of either claim 11 or claim 12 performed in absence of a digestive enzyme.

19. The method of either claim 11 or claim 12 wherein the tissue is cultured.

20. The method of either claim 11 or claim 12 wherein the tissue is engineered.

21. A method of ameliorating a damaged cartilage tissue in a mammal, comprising introducing into a damaged cartilage tissue in a mammal under conditions sufficient to ameliorate the damaged tissue a composition comprising a plurality of isolated particles sized from a viable tissue, the particles comprising cells having at least about 80% viability and cell-associated extracellular proteins organized in a matrix, each particle sized to have at least one dimension less than 60 µm, wherein microfracture is performed on bone adjacent the damaged tissue prior to introducing the particles.

22. The method of claim 21 further comprising thereafter adhering the composition to the damaged tissue.

23. The method of claim 21 further comprising adding thrombin to adhere the composition to the damaged tissue.

24. The method of claim 21 wherein the viable tissue is an engineered tissue.

25. The method of claim 21 wherein the viable tissue in the composition and the damaged tissue are the same type of tissue.

26. The method of claim 21 wherein the viable tissue in the composition and the damaged tissue are different types of tissue.

27. The method of claim 21 wherein the composition is introduced into the damaged viable tissue by a minimally invasive procedure.

28. A biocompatible implantable composition comprising a plurality of isolated biological tissue particles sized from juvenile cartilage, the particles in a matrix comprising chondrocytes having at least about 80% viability and chondrocytes-associated extracellular proteins, each particle sized to have at least one dimension less than 60 µm.

29. The method of claim 21 wherein the extracellular proteins are a component of an extracellular matrix.

30. The method of claim 21 wherein the isolated viable tissue particles comprise a plurality of isolated viable juvenile cartilage tissue particles.

31. The method of claim 21 wherein the particles are sized to have at least another dimension less than 1 mm.

32. The method of claim 21 wherein the viable tissue comprises hyaline cartilage or fibrocartilage.

33. The method of claim 21 wherein the particles include at least one of an adhesive, a buffer, or a bioactive agent.

34. The method of claim 21 wherein the viable tissue is allogenic.

35. The method of claim 21 wherein the viable tissue is cultured prior to introducing the particles.

36. The method of claim 24 wherein the viable tissue is engineered cartilage.

* * * * *